(12) United States Patent
Ross

(10) Patent No.: US 11,501,880 B1
(45) Date of Patent: Nov. 15, 2022

(54) ANONYMIZING GENETIC DATASETS IN A DISPARATE COMPUTING ENVIRONMENT

(71) Applicant: MASSACHUSETTS MUTUAL LIFE INSURANCE COMPANY, Springfield, MA (US)

(72) Inventor: Gareth Ross, Amherst, MA (US)

(73) Assignee: MASSACHUSETTS MUTUAL LIFE INSURANCE COMPANY, Springfield, MA (US)

( * ) Notice: Subject to any disclaimer, the term of this patent is extended or adjusted under 35 U.S.C. 154(b) by 908 days.

(21) Appl. No.: 16/216,770

(22) Filed: Dec. 11, 2018

Related U.S. Application Data

(60) Provisional application No. 62/597,824, filed on Dec. 12, 2017.

(51) Int. Cl.
| | |
|---|---|
| *G16H 50/30* | (2018.01) |
| *G16H 10/40* | (2018.01) |
| *G16B 20/20* | (2019.01) |
| *G16H 50/20* | (2018.01) |
| *G16B 5/20* | (2019.01) |
| *G16H 10/60* | (2018.01) |

(52) U.S. Cl.
CPC ............... *G16H 50/30* (2018.01); *G16B 5/20* (2019.02); *G16B 20/20* (2019.02); *G16H 10/40* (2018.01); *G16H 10/60* (2018.01); *G16H 50/20* (2018.01)

(58) Field of Classification Search
None
See application file for complete search history.

(56) References Cited

PUBLICATIONS

Chatzimichali, Eleni A., et al. "Facilitating collaboration in rare genetic disorders through effective matchmaking in Decipher." Human mutation 36.10 (2015): 941-949.*

* cited by examiner

*Primary Examiner* — G Steven Vanni
(74) *Attorney, Agent, or Firm* — Foley & Lardner LLP

(57) ABSTRACT

Disclosed is a method and a system for receiving a request to generate an anonymized pool dataset, wherein the request comprises overall number of people in the dataset, one or more genetic condition categories, a genetic attribute associated with each category, and a percentage of the number of users associated with each category; querying and receiving from a second server a set of datasets associated with people, wherein each dataset comprises health data associated with a user and a corresponding genetic data; generating a pool dataset from the anonymized set of datasets, wherein the pool dataset corresponds to the received overall number of users in the dataset, genetic condition categories, the genetic attribute associated with each category, and a percentage of the number of people in each category.

18 Claims, 5 Drawing Sheets

ANONYMIZING GENETIC DATASETS IN A DISPARATE COMPUTING ENVIRONMENT

CROSS-REFERENCE TO RELATED APPLICATIONS

This application claims priority to U.S. Provisional Patent Application Ser. No. 62/597,824, filed on Dec. 12, 2017, which is hereby incorporated by reference in its entirety.

TECHNICAL FIELD

This application relates generally to generating and manipulating datasets associated with efficient analytics processing.

BACKGROUND

Recent scientific improvements have made genome sequencing more accurate and easier to obtain. Scientists are now able to provide accurate data and insights as to genetic predispositions to different health conditions and forecast possible future health risks. Many institutions providing health-related services, however, are legally and technically prevented from using genetic data to determine a user's eligibility to enroll or determine a price structure for said health-related services. Because human mind is incapable of decoupling having access to certain data and anonymizing said data, many institutions have attempted to anonymize genetic (and other health-derived data) associated with their customers using computers. As the processing power of computers allow for greater computer functionality and the Internet technology era allows for interconnectivity between computing systems, many institutions utilize computer infrastructures to maintain/store genetic data associated with their customers. However, since the implementation of these more sophisticated computer infrastructures, several shortcomings in these technologies have been identified and have created a new set of challenges.

Existing and conventional methods, systems, and software solutions fail to provide fast and efficient anonymization due to a high volume of customer information existing on different networks and computing infrastructures. Managing such information on different platforms is difficult due to number, size, content, or relationships of the data associated with the customers. Therefore, there is a desire for a computing technology to address these challenges.

SUMMARY

For the aforementioned reasons, there is a need for a more efficient and faster system and method for processing large user datasets and generating anonymized datasets, which would allow institutions to anonymize genetically driven dataset a more efficient manner than possible with conventional computer data-driven analysis. There is a need for a network and computer-specific set of rules to produce efficient and accurate results when facing a high number of datasets.

Disclosed herein are systems and methods capable of addressing the above-described technical shortcomings. In an embodiment, a method comprises receiving, by a server from a client computing device, a request to generate an anonymized pool dataset, wherein the request comprises a number of users, a selection of at least one genetic condition category, a threshold corresponding to a genetic attribute associated with each genetic condition category, and a percentage of users associated with each genetic condition category; querying, by the server, a second server to receive a set of datasets corresponding to a plurality of users stored onto a database associated with the second server, wherein each dataset comprises data associated with each user comprising at least each respective user's genetic data; upon querying the second server, receiving, by the server, the set of datasets from the second server; generating, by the server, an anonymized set of datasets, wherein each dataset within the anonymized set of datasets corresponds to each user from the plurality of users, and wherein the anonymized set of datasets does not contain any identifiable information corresponding to any of the users; determining, by the server, which user within the anonymized set of datasets satisfies the threshold corresponding to the genetic attribute associated with each genetic condition category from the at least one genetic condition category; and generating, by the server, the anonymized pool dataset from the anonymized set of datasets, wherein the anonymized pool dataset comprises one or more users from users who satisfy the threshold, wherein a number of one or more users within the anonymized pool dataset corresponds to the number of users received from the client computing device, wherein each user from the one or more users is placed in the selected at least one genetic condition category that corresponds to each user's genetic data received from the client computing device, and wherein the number of users within each genetic condition category corresponds to the percentage of users associated with each genetic condition category received from the client computing device.

In another embodiment, a computer system comprises a first server in communication with a client computing device via a graphical user interface displayed on the client computing device, the graphical user interface generated by the first server; and a second server in communication only with the first server, wherein the first server is configured to: receive, from a client computing device, a request to generate an anonymized pool dataset, wherein the request comprises a number of users, a selection of at least one genetic condition category, a threshold corresponding to a genetic attribute associated with each genetic condition category, and a percentage of users associated with each genetic condition category; query a second server to receive a set of datasets corresponding to a plurality of users stored onto a database associated with the second server, wherein each dataset comprises data associated with each user comprising at least each respective user's genetic data; upon querying the second server, receive the set of datasets from the second server; generate an anonymized set of datasets, wherein each dataset within the anonymized set of datasets corresponds to each user from the plurality of users, and wherein the anonymized set of datasets does not contain any identifiable information corresponding to any of the users; determine which user within the anonymized set of datasets satisfies the threshold corresponding to the genetic attribute associated with each category from the at least one genetic condition category; and generate the anonymized pool dataset from the anonymized set of datasets, wherein the anonymized pool dataset comprises one or more users from users who satisfy the threshold, wherein a number of one or more users within the anonymized pool dataset corresponds to the number of users received from the client computing device, wherein each user from the one or more users is placed in the selected at least one genetic condition category that corresponds to each user's genetic data received from the client computing device, and wherein the number of users within each genetic condition category corresponds to the percentage of users associated with each genetic condition category received from the client computing device.

It is to be understood that both the foregoing general description and the following detailed description are exemplary and explanatory and are intended to provide further explanation of this disclosures and claims.

BRIEF DESCRIPTION OF THE DRAWINGS

The accompanying drawings constitute a part of this specification and illustrate an embodiment of this disclosure and together with the specification, explain the disclosure.

DETAILED DESCRIPTION

Figure 1:
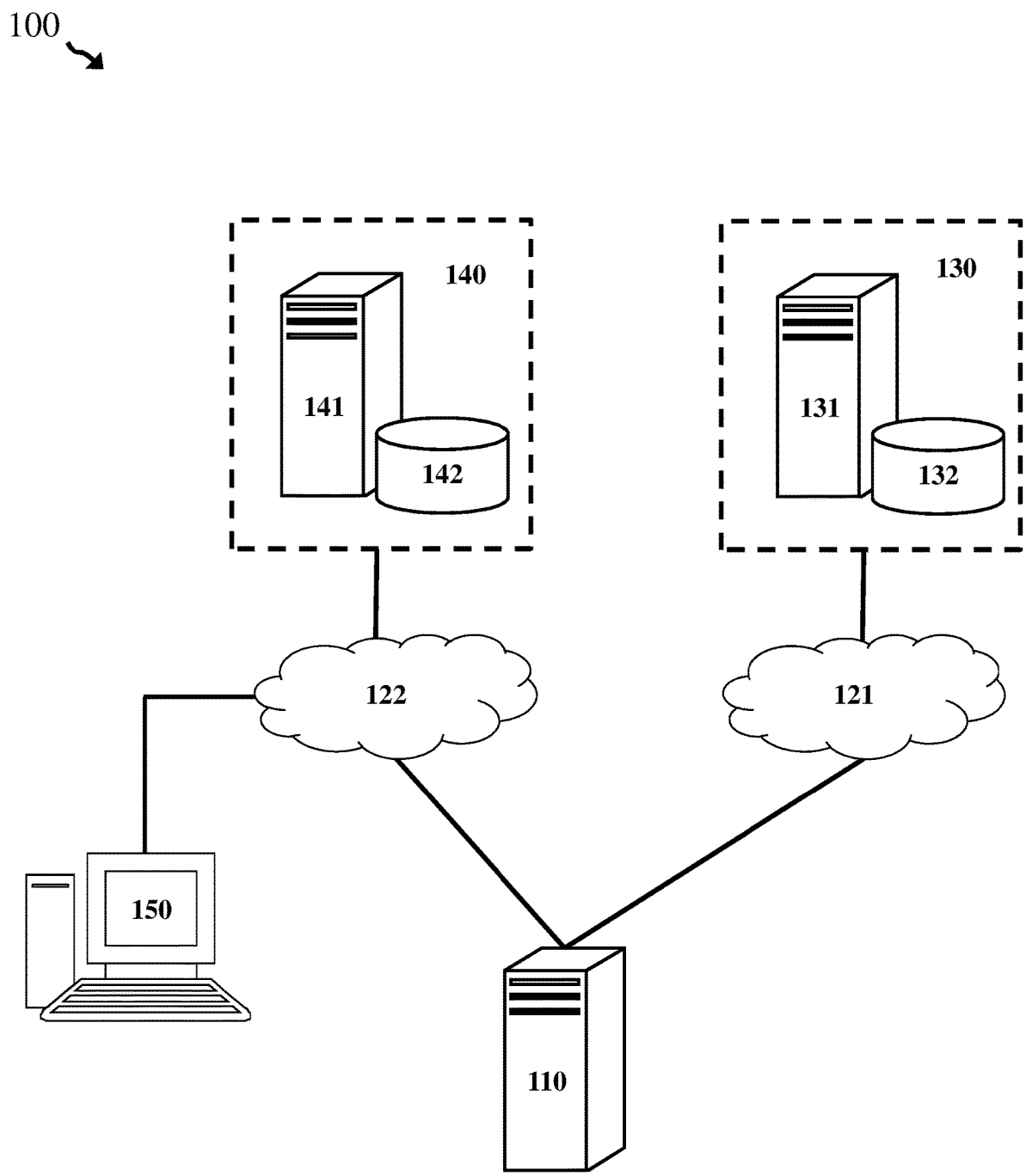
FIG. 1 illustrates an example of a system for generating an anonymized genetic dataset, according to an embodiment.

Reference will now be made to the exemplary embodiments illustrated in the drawings, and specific language will be used here to describe the same. It will nevertheless be understood that no limitation of the scope of the disclosure is thereby intended. Alterations and further modifications of the embodiments within this disclosure, which would occur to a person skilled in the relevant art and having possession of this disclosure, are to be considered within the scope of this disclosure.

FIG. 1 illustrates components of a system 100, according to an exemplary embodiment. The system 100 comprises an analytics server 110, a database server 131 and a database 132 of an institution 130 (e.g., a second institution), a database server 141 and a database 142 of an institution 140 (e.g., a first institution), communication network 121-22, and a client device 150. The client device 150 may communicate with the analytics server 110 via the communication network 122, such as the Internet or any other public or private network. The client device 150 may also be in connection with the institution 130 or the institution 140 via the analytics server 110. The client device may also be in connection (or be a part of) the institution 140 directly via the network 122. For example, an administrator associated with the institution 140 may operate the client device 150.

In operation, the client device 150 may request the analytics server 110 to derive various forms of analytical information from the data records of the database 142 and/or 132 (e.g., databases associated with the institutions 130 and or the institution 140). The client device 150 may be associated with the either of the institutions and may be prevented from accessing raw data from either of the databases (132 and/or 142). For example, the client device 150 may be operated by an administrator or a client of the institution 140 and may be limited to anonymized and derived data from institution 130. In some embodiments, the client device 150 is prevented to directly access any computing device associated with the institution 130. In those embodiments, the client device 150 may only communicate with the server 131 and database 132 via the analytics server 110.

The database 132 may store data records that are associated with several users, where the data records each contain at least one field identifying which user account was associated with a particular data field. The database 132 may store personal attributes and genetic data associated with each user such as name, user identifiers (e.g., Social Security numbers, Driver's license number, or other identifiers), age, height, weight, and the like. The database 132 may store data records generated, stored, and/or received by the database server 131. The database 132 may receive user attribute data from an electronic interaction with the users; for example, the server 131 may provide an online accessible graphical user interface configured to receive personal attributes associated with the user. The database 132 may also receive user attribute data from the analytics server 110, server 141, and/or a third-party server (not show). The database 132 may also receive genetic data associated with each user from a third-party server. For example, the institution 130 may provide genetic analytics services to a variety of users via collecting the users' physical sample and performing genetics analysis.

The institutions 130 may acquire genetic data associated with the physical sample from the users and analyzed a third-party lab (or the institution 130 itself). The database 132 of the institution 130 (via server 131) may receive the users' genetic data and/or the analyzed biological and genetic parameters from a third-party lab. Non-limiting examples of the biological parameters can include bioanalytic parameters and biometric parameters. The bioanalytic parameters can include one or more of qualitative and quantitative measurements of xenobiotics and biwotics in tissues and body fluids of the users. The biometric parameters can include one or more qualitative and quantitative measurements of physical attributes of the users. The physical attributes of the users can also include one or more of DNA, fingerprints, facial features, voice patterns, retinal or iris patterns of the users. In some embodiments, the user attributes comprise DNA analysis. For example, the institution 130 may analyze the user's physical sample to determine a sequence of single nucleotide polymorphisms (SNP) associated with each user. SNPs are the most common type of genetic variation among different users. Each SNP represents a difference in a single DNA building block (e.g., nucleotide). For example, a SNP may replace the nucleotide cytosine (C) with the nucleotide thymine (T) in a certain stretch of DNA. SNPs occur normally throughout a person's DNA. They occur once in every 300 nucleotides on average; therefore, there are approximately 10 million SNPs in the human genome. Most commonly, these variations are found in the DNA between genes. A SNP can act as biological marker for each user. When SNPs occur within a gene or in a regulatory region near a gene, they may play a more direct role in a particular disease by affecting the gene's function. Some SNPs have no effect on health or development. For example, rs12913832 is a SNP near the OCA2 gene that may be functionally linked to blue or brown eye color, due to a lowering of promoter activity of the OCA2 gene; in another example a rs12913832-T SNP correlates to brown eyes.

Some of the above-described genetic differences have proven to be very important in the study of human health. Some SNPs may help predict an individual's response to certain drugs, susceptibility to environmental factors (such as toxins), and risk of developing particular diseases. SNPs can also be used to track the inheritance of disease genes within different families. Some SNPs have been associated with complex diseases such as heart disease, diabetes, and cancer. For example, BRCA1 and BRCA2 are human genes that produce tumor suppressor proteins. These proteins help repair damaged DNA and, therefore, play a role in ensuring the stability of the cell's genetic material. When either of these genes is mutated, or altered, such that its protein product either is not made or does not function correctly, DNA damage may not be repaired properly. As a result, cells are more likely to develop additional genetic alterations that can lead to cancer. Specific inherited mutations in BRCA1 and BRCA2 increase the risk of female breast and ovarian cancers, and they have been associated with increased risks of several additional types of cancer. Together, BRCA1 and BRCA2 mutations account for about 20 to 25 percent of hereditary breast cancers and about 5 to 10 percent of all breast cancers. In addition, mutations in BRCA1 and BRCA2 account for around 15 percent of ovarian cancers overall. Breast and ovarian cancers associated with BRCA1 and BRCA2 mutations tend to develop at younger ages than their nonhereditary counterparts. A harmful BRCA1 or BRCA2 mutation can be inherited from a person's mother or father. Each child of a parent who carries a mutation in one of these genes has a 50 percent chance of inheriting the mutation. The effects of mutations in BRCA1 and BRCA2 are seen even when a person's second copy of the gene is normal. Therefore, a genetic study of the users may lead to discovery of their predispositions to different diseases and may provide a well-rounded health risk assessment associated with the users.

The institution 130 (via the server 131) may receive values associated with each user's genetic sequencing analysis and store said data in the database 132. The database 132 may be hosted on any number of computing devices comprising a non-transitory machine-readable storage medium capable of storing data records received from the database server 131, and in some cases, received from the analytics server 110, or other computing devices (e.g., public websites or cloud service providers). The database 132 may further comprise a processor capable of executing various queries and data record management processes, according to instructions from the analytics server 110 or the database server 131. The database 132 may be the same computing device as the server 131, or be hosted on a distinct computing device that is in networked-communication with the analytics server 110.

The server 131 may communicate data records and instructions to and from the analytics server 110, where the data records may be stored into the database 132 and where various analytics may be performed on the data by the database server 131 in accordance with the instructions from the analytics server 110 or (indirectly by the client device 150). The server 131 may be any computing device comprising a processor capable of performing the various tasks and processes described herein. Non-limiting examples of a database server 131 may include a server, desktop, laptop, tablet, and the like. The database server 131 comprises any number of computer-networking components (e.g., network interface card) that facilitate inter-device communications via the communication network 121. There may be any number of distinct computing devices functioning as the server 131 in a distributed computing environment. The server 131 may host an online service, such as cloud-computing application service, an online shopping site, or any other service that provide customer-facing web-based applications that collect customer data through web-based transactions with the client device 150 over one or more networks such as the communication network 121.

The institution 140 may be an institution that provides health-related services to the users. For example, the institution 140 may be an insurance company that provides different insurance services to the users. As described above, the institution 140 may be prevented from accessing the users' genetic data (e.g., genetic data stored in the database 132). The database 142 may contain any data associated with the users (e.g., services provided to the users, biometric data, and the like) and may be hosted on any number of computing devices comprising a non-transitory machine-readable storage medium capable of storing data records received from the server 141, and in some cases, received from the analytics server 110, the client device 150, or other computing devices (e.g., public websites or cloud service providers). The database 142 may further comprise a processor capable of executing various queries and data record management processes, according to instructions from the analytics server 110 or the database server 141.

The database 142 may be the same computing device as the server 141, or be hosted on a distinct computing device that is in networked-communication with the analytics server 110. The database server 141 may communicate data records and instructions to and from the analytics server 110, where the data records may be stored into the database 142 and where various analytics may be performed on the data by the database server 141 in accordance with the instructions from the analytics server 110 or (indirectly by) the client device 150 via network 122. The database server 141 may be any computing device comprising a processor capable of performing the various tasks and processes described herein. Non-limiting examples of a server 141 may include a server, desktop, laptop, tablet, and the like. The server 141 comprises any number of computer-networking components (e.g., network interface card) that facilitate inter-device communications via the communication network 122. There may be any number of distinct computing devices functioning as the server 141 in a distributed computing environment. The server 141 may host an online service, such as cloud-computing application service, an online shopping site, or any other service that provide customer-facing web-based applications that collect customer data through web-based transactions with the client device 150 over one or more networks such as the communication network 122.

The analytics server 110 may perform various analytics on data records stored in the database 131 and/or 141 and transmit the results to the client device 150. The analytics server 110 may be any computing device comprising a processor capable of performing the various tasks and processes described herein. Non-limiting examples of the analytics server 110 may include a server, desktop, laptop, tablet, and the like. The analytics server 110 comprises any number of computer-networking components, which facilitate inter-device communications via the communication network 121 and/or 122. There may be any number of distinct computing devices functioning as the analytics server 110 in a distributed computing environment.

A client device 150 may access a web-based service or application hosted by a database server 141, from which customers may provide various types of personal and/or confidential data that may be stored in the database 142. The client device 150 may be any computing device comprising a processor capable of performing the various tasks and processes described herein. Non-limiting examples of a client device 150 may include a server, desktop, laptop, tablet, and the like. The client device 150 comprises any number of computer-networking components (e.g., network interface card) that facilitate inter-device communications via the communication network 122. Although the communication network 121 and 122 are shown as separate and distinct communication networks, in some embodiment, a single communication network may provide services (e.g., connect the computing devices described in FIG. 1).

Figure 2:
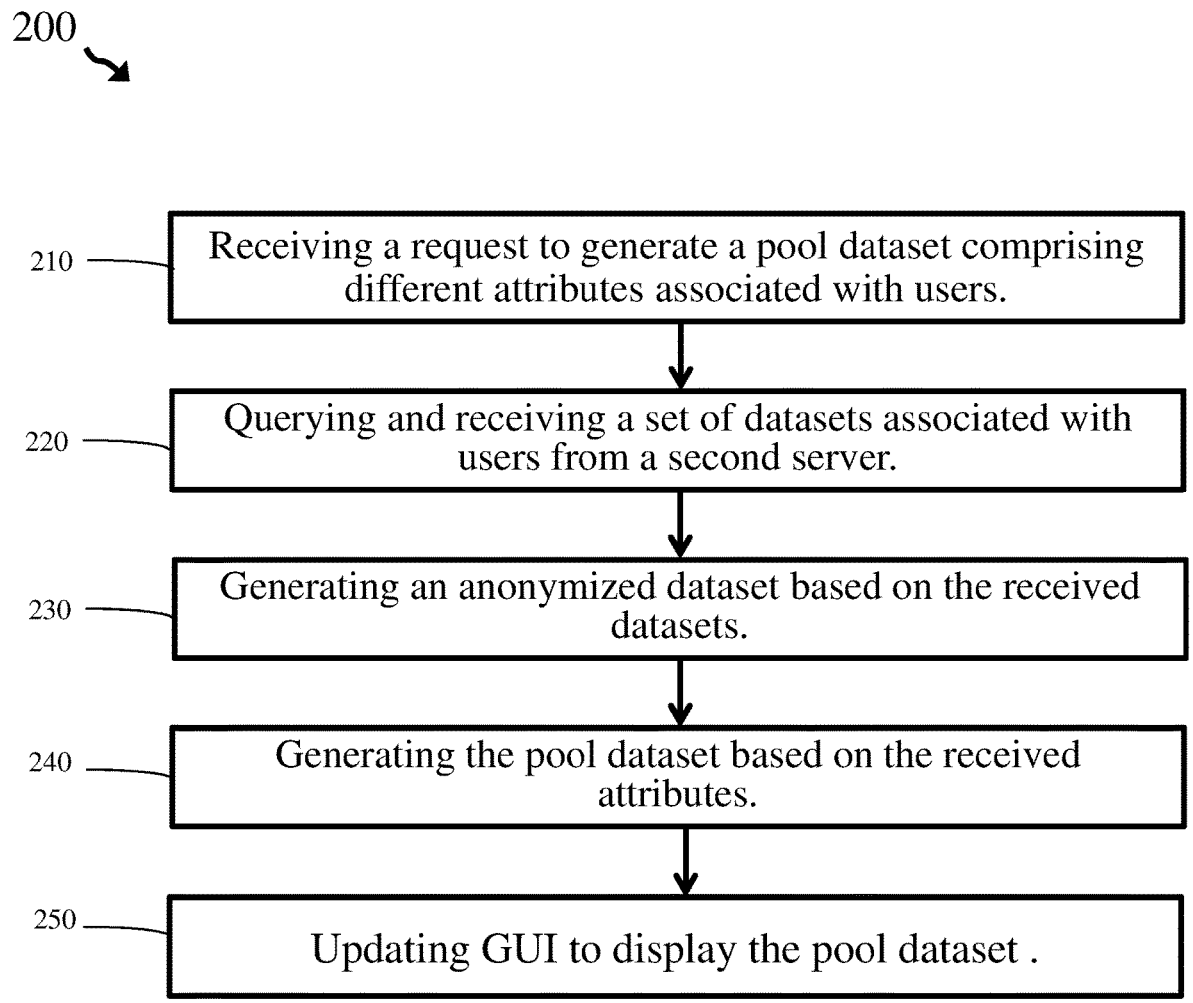
FIG. 2 illustrates a flowchart depicting operational steps of a method for generating an anonymized genetic dataset, according to an embodiment.

Referring now to FIG. 2, a flowchart depicting operational steps of a method for anonymizing and generating a pool dataset is illustrated in accordance with an embodiment. Steps of the method 200 may be implemented using one or more modules of the analytics server, the client device, and two different institutions. FIG. 2 does not imply any limitations with regard to the environments or embodiments that may be implemented. Modifications to the depicted environment or embodiment shown in FIG. 2 may be made.

At step 210, the analytics server may receive, from a client computing device, a request to generate a pool dataset, wherein the request comprises a number of users, a selection of at least one genetic condition category, a threshold corresponding to a genetic attribute associated with each genetic condition category, and a percentage of users associated with each genetic condition category. The analytics server may generate a graphical user interface (GUI) (e.g., a website) comprising a set of input fields and configured to be displayed on the client device. For example, the GUI can include an electronic form for completion by an administrator operating the client device, where the electronic form includes a plurality of graphical elements (e.g., text fields, buttons, sliders, checkboxes, dropdown menus, and the like) for interaction with the client, and where the electronic form may be associated with a profile corresponding to the users (e.g., users to whom an institution associated with the client device provided health-related service). The analytics server may host a website accessible to the end-users (e.g., administrator operating the client device), where the content presented via the various webpages may be controlled based upon each particular end-user's role. In the illustrative embodiment, the GUI presents a request generation screen that allows an input via a graphical element by the client computing device of a value representing number of users, a selection of at least one category from a set of categories, and a percentage value representing a percentage of users associated with each genetic condition category. Upon the client computing device inputting information into the GUI and transmitting the information to the analytics server, the analytics server may query a database associated with an institution (such as institution 140) and provide a lists of all the users stored in a database associated with the institution (e.g., database 142) and update the GUI to display the data associated with the users.

In an example, the administrator (operating the client device) may log into the website provided by the analytics server and request the analytics server to generate a pool dataset. The pool dataset may refer to a selection of all users based on their corresponding health-related data (e.g., genetically sorted). The analytics server may also receive (via the GUI) user attributes, number of users, and distribution attributes associated with the users within the pool dataset. For example, the administrator may request a pool dataset of 500 users within the age range of 25-35. The administrator may also request the pool dataset to comprise 70% of users pre-disposed to heart disease and 30% not predisposed to heart disease.

In other embodiments, the administrator can customize the pool dataset by modifying any of the above-mentioned attributes. For example, the pool dataset may be customized by modifying the users by any of their attributes (age, height, weight, income, cholesterol level, blood pressure, and the like) or any specific genetic characteristic (e.g., users with specific SNP characteristic, users who are more likely to have heart attacks, users who have the BRCA2 SNP, and the like). Additionally or alternatively, the pool dataset can also be customized to have multiple genetic condition categories. For example, a pool dataset may comprise 20% of low genetically pre-disposed heart disease probability (category A), 30% with moderate genetically pre-disposed heart disease probability (category B), 40% with sever genetically pre-disposed heart disease (category C), and 10% of no genetically pre-disposed heart disease (category D).

At step 220, the analytics server may query a second server to receive a set of datasets associated with the users, wherein each dataset comprises data associated with a user and a corresponding genetic data. The analytics server may query and search for all the users and their corresponding data (biometric, genetics, or other data). In some embodiments, the analytics server may limit the query in accordance with the received attributes from the client device and to the users associated with a first institution. For example, if the requested pool dataset requires the users to be within 25-35 years of age, the analytics server may also limit the query to all users within the said age range. The analytics server may also only query for the users associated with the institution associated with the client device.

Figure 3:
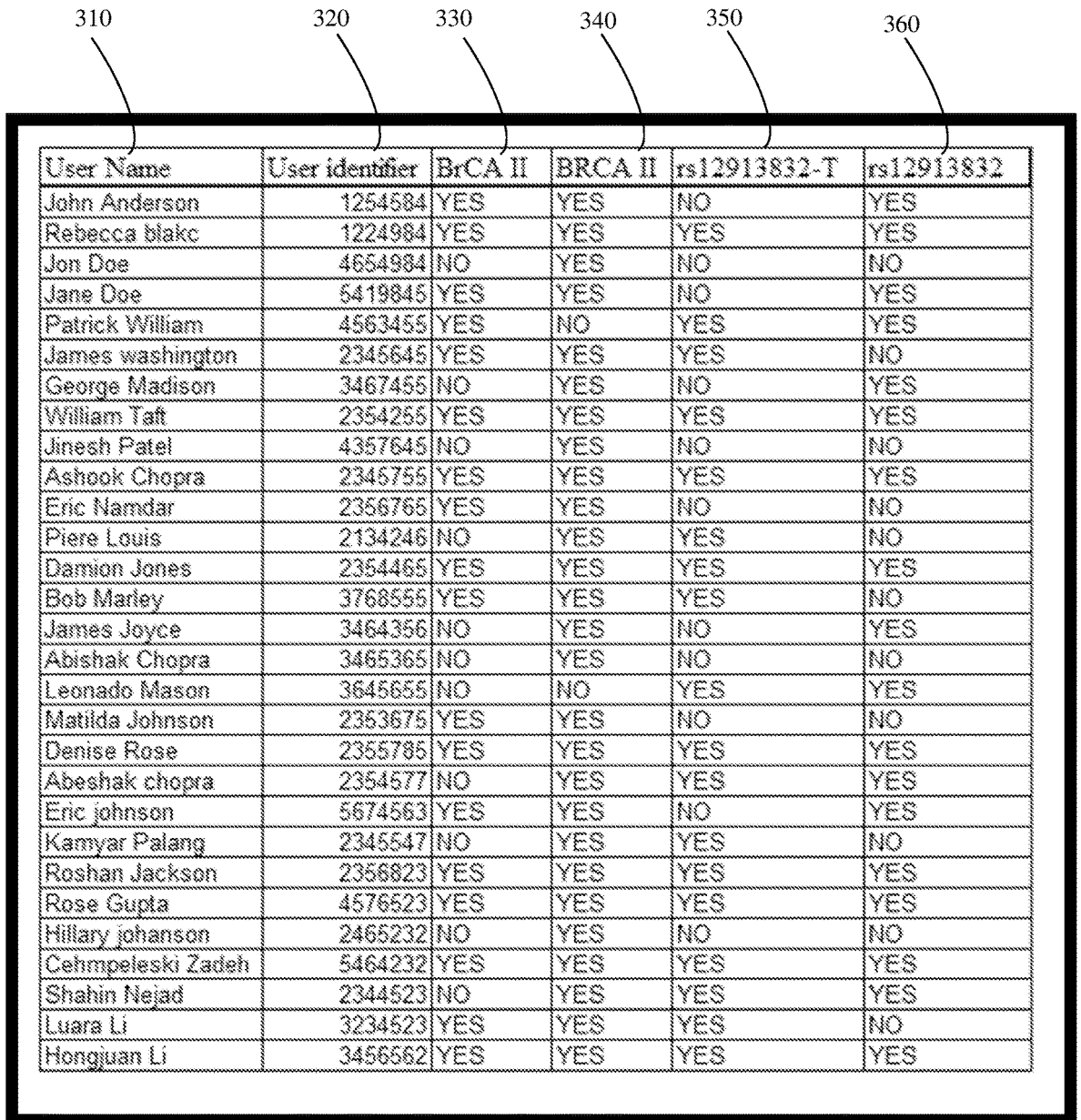
FIG. 3 illustrates a user genetic health-related dataset received from a second institution, according to an embodiment.

For example (and referring to FIG. 1), if the analytics server receives the request to generate a pool dataset from client device 150 (which is associated with the institution 140), the analytics server may query the database of the institution 130 to receive users that are associated with the institution 140 (e.g., customers of the institution 140). Upon querying the second database, the analytics server may receive a dataset comprising of all users and corresponding relevant data from a second institution. A non-limiting example to illustrated this step may include the analytics server querying the database 132. FIG. 3 illustrates a user dataset received from the second institution, according to an embodiment. The analytics server may receive dataset 300 from the second institution. Dataset 300 may include user identifications (e.g., user name 310 and user identifier 320) and different genetically driven data (e.g., genetic condition categories 330-360). For instance, BRCA1 and BRCA2 indicate an increased risk of breast cancer. Therefore, genetic condition category 330 indicates whether a user is at a higher risk of developing breast cancer.

Figure 4:
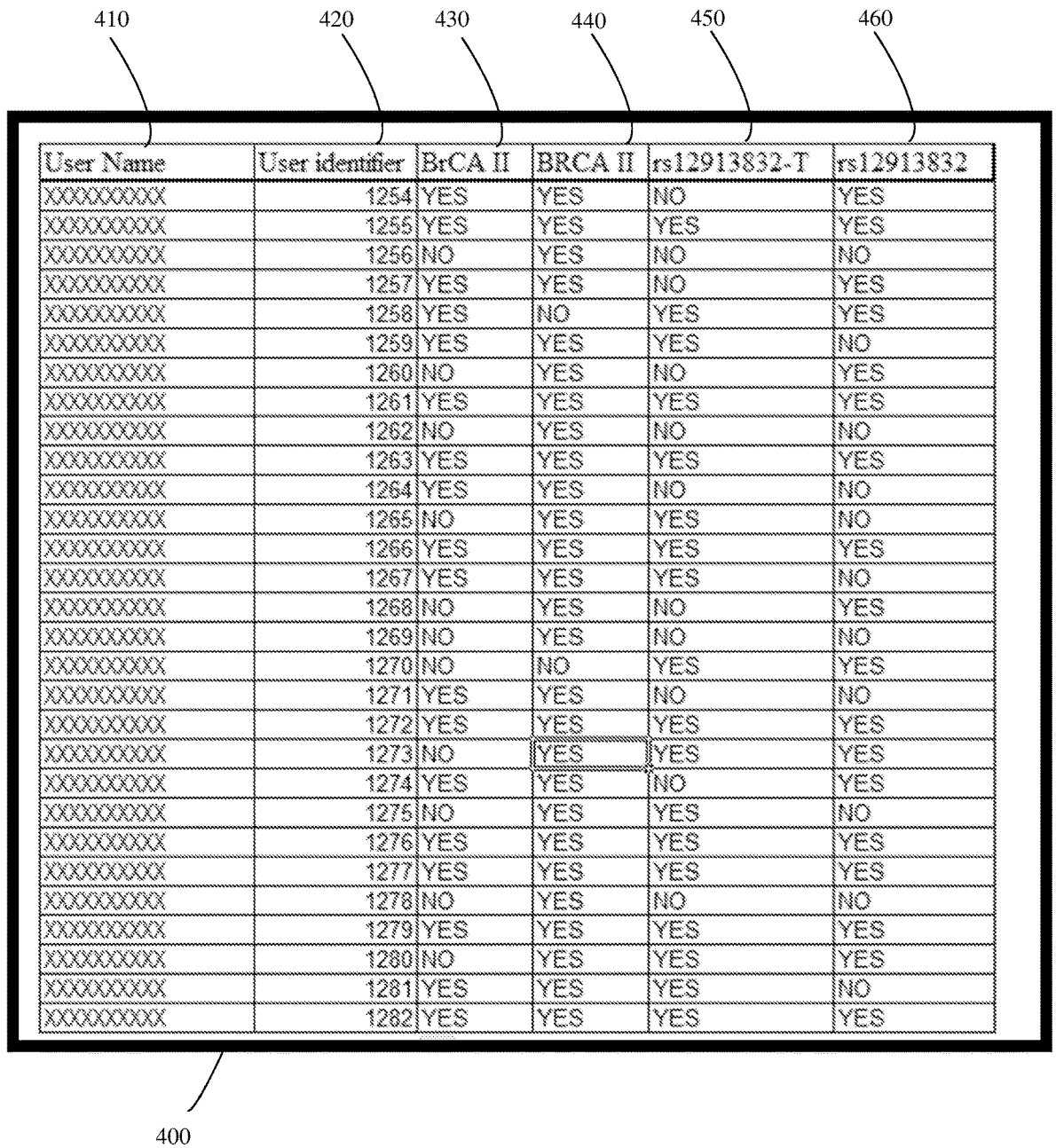
FIG. 4 illustrates an anonymized dataset, according to an embodiment.

At step 230, the analytics server may generate a second set of datasets, wherein each dataset within the second set of dataset corresponds to each first dataset, wherein the second dataset comprises a randomly generated value associated with the data associated with each use of the first set of datasets and the corresponding genetic data. The analytics server may anonymize the user datasets (received in step 220) in order to prevent the first institution (e.g., the institution associated with the client device) from learning about users' identities and their specific information. In an embodiment, the analytics server may assign a randomly generated value to each user, assign a different identifier, assign random names to the user, or modify the existing user identifiers by removing a portion of their identifiers (e.g., using only the last 4 digits of the user identifiers). FIG. 4 illustrates an anonymized dataset generated by a second institution, according to an embodiment. The analytics server may generate dataset 400 by anonymizing dataset 300

(illustrated in FIG. 3). For example, the analytics server anonymizes the user name 410 and the user identifier 420.

At step 240, the analytics server may generate a pool dataset from the second set of datasets, wherein the pool dataset corresponds to the received overall number of users in the dataset, one or more genetic condition categories, an attribute associated with each genetic condition category, and a percentage of the number of people in each genetic condition category. The analytics server may generate the pool dataset using the attributes received from the client device (step 210). In some embodiments, the pool dataset is completely anonymous and the analytics server may remove any identifying information associated with the users. The analytics server may generate the pool dataset using the attributes received from the client device (step 210).

Figure 5:
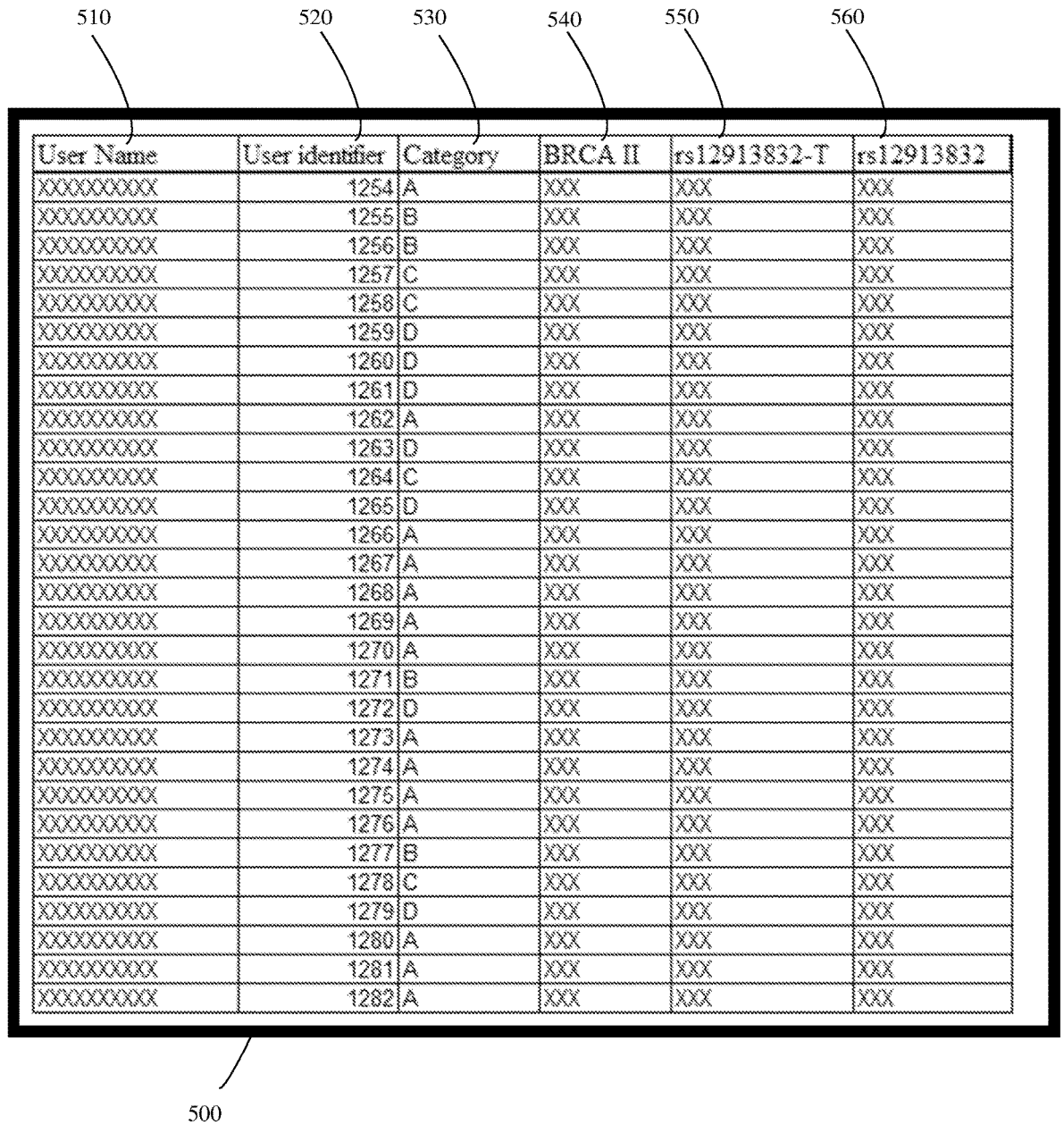
FIG. 5 illustrates a pool dataset, according to an embodiment.

At step 250, the analytics server may update the GUI to display the pool dataset. The analytics server may display the pool dataset on the client device or may use other electronic forms (e.g., email or other transmittal means) to transmit the pool dataset to the administrator operating the client device. FIG. 5 illustrates a generated pool dataset generated according to an embodiment. The analytics server may display the pool dataset 500. The pool dataset 500 may comprise an anonymized (e.g., by redacting or by assigning a randomly generated user identifiers) the user name 510, user identifier 520, and genetically driven information (e.g., categories 540-560). The analytics server may also generate a health-related genetic condition category (e.g., category 530) corresponding to the received attributes in step 210. Pool dataset 500 includes 30 users and corresponds to each user's predisposition to heart disease. Pool dataset 500 includes 4 categories (e.g., low pre-disposition to heart disease or category A, moderate pre-disposition to heart disease or category B, sever pre-disposition to heart disease or category C, and no pre-disposition to heart disease or category D), as illustrated in FIG. 5, 50% of the users within the pool dataset 500 belong to category A, 12.5% of the users within the pool dataset 500 belong to category B, 12.5% of the users within the pool dataset 500 belong to category C, and 25% of the users within the pool dataset 500 belong to category D.

In some embodiments, the analytics server may determine a genetically derived mortality value and generate the pool dataset based on genetically derived mortality values associated with each user. For instance, the analytics server may execute one or more artificial intelligence computer models to identify common identifiers/factors among the users within the anonymized pool dataset. For instance, by executing the AI model, the analytics server may identify that all the users within the anonymized pool dataset share a cholesterol level that is within a certain range.

The analytics server may generate and submit a feature vector associated with each user including their health data (e.g., genetics data and other data stored in database 131, as illustrated in FIG. 1). The analytics server may generate the feature vector based on the anonymized dataset (as described above) and submit it to an application programming interface (API) hosted on an application server associated with (e.g., hosted by) the server of the first institution (e.g., server 141 illustrated in FIG. 1). In pattern recognition and machine learning, a feature vector is an n-dimensional vector of numerical features that represent an object. Many algorithms in machine learning require a numerical representation of objects because such representations facilitate processing and statistical analysis. Simply put, a feature vector is a representation of each user and comprises at least the user identifier (e.g., anonymized identifier) and health data (e.g., genetic information derived using the physical sample provided by each user). In some embodiments, the feature vector may also include other non-genetic data (e.g., height, weight, exercise pattern, cholesterol, and the like). Each user may be represented by one feature vector.

The database server of the first institution may host a DBMS and an in-memory database managed via the DBMS. The in-memory database stores a set of model records, where each of the model records stores a field containing a model. Additionally or alternatively, a set of records define the model when the set of records is aggregated, such as via the DBMS or the application server, and then processed (e.g., via the DBMS) or the application server, such that the model is created or formed thereby. Accordingly, the analytics server may select a model record from the set of model records via the DBMS and may also retrieve the model therefrom. The analytics server may then insert the model into the application for processing for use with the feature vector. The analytics server may apply the feature vector to the mortality model in the application running on the application server. The model may then analyze the feature vector and the analytics server may receive a mortality score from the data server of the first institution. Even though, this embodiments, depicts an example where the mortality model is stored within a database of the first institution, in other embodiments, the mortality model may be stored in the second other databases (e.g., a third party database, database associated with the analytics server or the second institution).

The mortality model may be generated by the first institution using known data records associated with users (previous or present) or other third-party provided information. Each of the user records may contain a set of discrete observation values about a particular user, such as what a user risk profile looks like at a certain point in time. Such information can be obtained from a set of inputs received from a set of users relating to a specific data point associated with the users, such as a question answered by the user, a service requested by the users, a result of a panel of biochemical and genetic lab tests based on physical samples obtained directly from the users, a motor vehicle record, and others. Likewise, each of the user records may contain a survival information, such as numerical data, which varies through time until a death event is recorded for that record.

In an illustrative example, the mortality risk is learned from a set of health and behavioral variables extracted from the set of complete data, such as the set of user records. Some of such variables may be integrated into a mortality mode. For example, such variables include at least one of genetic data including genome sequencing data, age, whether the user smoked in previous 5 years, blood disorder, medical diagnostic test in previous 5 years, gamma glutamyltransferase, aspartate transaminase (AST) and alanine transaminase (ALT) ratio, urine based nicotine metabolites, globulin, taking prescription drugs, blood urea nitrogen, creatinine, urine total protein, alkaline phosphatase, hemoglobin, systolic blood pressure, disability claim in previous 5 years, diastolic blood pressure, motor vehicle violations in past, estimated glomerular filtration rate, glucose, anti-HCV (hepatitis C), vascular disorders, cholesterol, triglycerides, urine specific gravity, urine, respiratory disorders, cocaine metabolites, albumin globulin ratio, urine creatinine, high density lipoprotein, mental disorders, family history of diabetes, family history of vascular disorders, pulse at rest, urine glucose, diabetes, height, prostate specific antigen, weight, cancer disorder, serum glutamic oxaloacetic transaminase AST, body mass index, total bilirubin, family history of cancer, serum glutamic-pyruvic transaminase ALT, urine pc ratio, fructosamine, HIV positive, prescription drug history (derived from prescription drug databases), credit risk history, physical activity history (derived from sensor data), or medical examination history (derived from EMR and PHR data).

This set of user records is periodically updated to include survival information for each of the users and to an extent that new data points for the set of user records is received. For example, a user's data record may be updated using new health data (e.g., a new disease diagnoses) or by web crawling different database (e.g., social networking databases or health related databases). Furthermore, for a set of risk models stored in an in-memory database (such as the database 141 or 131 illustrated in FIG. 1) a health-related model re-learning process is performed, such as via a combination of a cost regression (linear model appearing as a linear regression where inputs are data points, as disclosed herein, and are fit to a response variable that indicates a survival time and leaf squares are performed to quantify an error and a gradient is dispensed to optimize a function) and a random survival forest (a collection of decision trees, where a number of trees and a depth of trees is compared and optimized as data changes/updated, such as the set of user records), where a prediction that is output from the combination are input into another cost regression model to get a risk score value.

In the random survival forest, for each tree built, a variable is chosen from a subset of all variables available that maximizes a particular test statistic that summarizes survival between at least two groups. For example, if age is chosen as a splitting variable/threshold, then the age splits the set of user records set into two groups: one group that has an age less than that threshold and another one that has one greater. The age is chosen such that a survival characteristic of those two groups, i.e., a difference between the two groups, is maximized. This difference is quantified through a long-range statistics that is computed via comparing a Kaplan—Meier estimator between a survival curve of the two groups. Resultantly, as the set of user records is updated, a search is performed over all different combinations of the number of trees and the depth of trees to find a combination that maximizes a particular performance metric that is being used for quantification.

Since each tree is going to maximize the metric, but an exact number of how many trees and the depth of trees is unknown, various iterations/traversals/searches are performed, i.e., a vast search (end by end metric or M by M) over all different combinations and you choose a combination that maximizes a particular performance statistic, such as concordance (a probability of ranking a pair of observations according to which one dies first or which, you know, which one is the most likely to die first). For example, for two records of the set of user records, one of two records corresponds to a deceased individual and the other of the two records corresponds to somebody that is still living, then the dead individual may be ranked first and the still living individual may be second. For example, same methodology may apply if, for two records of the set of user records, one individual or both individuals are deceased, then the two records are ranked according to which one deceased first. A fraction of time this is performed correctly corresponds to a concordance which can be interpreted as a probability of selected the first deceased correctly. Note that although a tree can be maximized for a particular metric, such as under ten thousand iterations in about twenty-four hours, in some implementations, multiple metrics can be maximized for.

Such intense processing (e.g., requiring a high amount of computing power) cannot be manually performed. Even if a health-related variable could be manually processed in isolation (e.g. determine how the risk variable varies with a risk, such as with a mortality risk, and then a point value is subjectively assigned to that based on how important that subjectively is and then move to a next point and so on), in contrast, various data structure methods, as disclosed herein, such as tree-based processing, a set of conditional probabilities or conditional risks is generated that is based on hundreds of interactions between different types of variables that are observed on a particular individual at a particular point in time, as memorialized in that user record. When performed by conventional computing devices and using the conventional brute force method (e.g., calculating each permutation and each variable separately and aggregating the data), the above-mentioned calculations are extremely time-consuming and require a very high computing power. However, using the methods and the computer infrastructure, presented herein, may reduce the computing power needed or time consumed to achieve the same and/or better results.

Stated differently, historical health-related assessments have looked at each variable independently of all others and assigned a score or a weighting to that variable. Then, the next variable is independently examined and so on until all relevant data points have been exhausted. Then, all the examined data points are summed up, i.e., points that are assigned for falling in different ranges for each one of those variables. In contrast, a holistic score is automatically generated that learns what kinds of dependencies or interactions exist amongst those variables and how they correlate with risk. For example, in context of risk assessment, traditionally, assuming one is trying to minimize points to correspond to lower risk, fewer points are assigned to user records/profiles for older users than for users of any age who have high cholesterol. However, in a mortality model as applied to a particular user record, as disclosed herein, upon examination of each of such variables, such as age and cholesterol, and upon examination of a distribution of having a low age and a high cholesterol, a risk value may be determined that for that particular user record the risk value may actually be low. Whereas, if one analyzes ages and cholesterol in isolation, then a higher risk value may be assigned (note that opposite or different kinds of dependencies amongst all various relevant variables can be possible).

For example, a data model may include various data trees and then generate an average across the data trees, where conditional dependencies can be built after running through a tree, scan values of variables, and then scan the values of user records that are flagged as alive or dead, and then runs through a subsequent tree; and then uses a new variable to split the prior tree into the sub-tree. Consequently, the user records can be grouped according to likelihood of mortality by a variable (e.g., age) because age is a good indicator of alive/dead in the dataset, and then a next variable (e.g. cholesterol) can be used to identify when the next variable becomes a good indicator of breaking group into alive or dead; automatically breaks the group up using a log-rank test to determine whether there is a good indicator to break up groups; as preferred to choose a value that maximizes the log rank score for the survival score to do a split. This may be done via running through datasets of clients or publicly available or proprietary databases (LexisNexis queries) for labeled dataset.

As a non-limiting example, the genetic data may be used for underwriting purposes. The first institution may be an insurance company. The first institution may provide health-related services. The first institution may incentivize customers by offering a discount rate for enrolling in a genetic study performed by the second institution. The first institution, however, may not use the customers' genetic data for underwriting purposes. The first institution may employ another institution that is capable of performing genetic studies (e.g., the second institution). The customers may provide a physical sample to the second institution. The second institution may perform genetic studies and determine different genetic predispositions associated with the customers. The analytics server may receive the genetic results from the second institution, anonymize the dataset, and generate a new dataset (e.g., pool dataset) based on attributes received from the first institution to be presented to the first institution. The pool dataset may be anonymized (e.g., the analytics server may remove any personal identification information from the pool dataset) and may comprise a large number of customers in different genetically driven pools and categories (e.g., low heart disease category, medium heart disease category, and high heart disease category). By presenting a pool of users to the first institution, the anonymity of the customers will be preserved, as individual genetic data is nearly impossible to be traced back to each individual user. The first institution may then use the anonymized pool dataset to re-negotiate different terms and conditions associated with the health-related services provided to each of the user within the pool dataset.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of this disclosure. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A method comprising:
receiving, by a server from a client computing device, a request to generate an anonymized pool dataset, wherein the request comprises a number of a first set of users from which to generate the anonymized pool dataset, a selection of at least one genetic condition category, a threshold corresponding to a genetic attribute associated with each genetic condition category, and a percentage of the first set of users associated with each genetic condition category;
querying, by the server, a second server to receive a set of datasets corresponding to the first set of users stored onto a database associated with the second server, wherein each dataset comprises data associated with each user comprising at least each respective user's genetic data, wherein the client computing device is prevented from communicating with the second server;
upon querying the second server, receiving, by the server, the set of datasets from the second server;
generating, by the server, an anonymized set of datasets, wherein each dataset within the anonymized set of datasets corresponds to each user from the first set of users, and wherein the anonymized set of datasets does not contain any identifiable information corresponding to any of the first set of users;

executing, by the server, a trained machine-learning model to identify each dataset within the anonymized set of datasets that satisfies the threshold corresponding to the genetic attribute associated with each genetic condition category from the at least one genetic condition category;

generating, by the server, the anonymized pool dataset from the anonymized set of datasets, wherein the anonymized pool dataset comprises a second set of users from the first set of users who satisfy the threshold, wherein a number of the second set of users within the anonymized pool dataset corresponds to the number of the first set of users from which to construct the anonymized pool dataset received from the client computing device, wherein each user from the second set of users is placed in the selected at least one genetic condition category that corresponds to each user's genetic data received from the client computing device, and wherein the number of the first set of users within each genetic condition category corresponds to the percentage of the first set of users associated with each genetic condition category received from the client computing device; and transmitting, by the server, the anonymized pool dataset to a third server configured to determine a mortality value associated with each user within the anonymized pool dataset and associated with the genetic attribute of each genetic condition category.

2. The method of claim 1 further comprising, upon transmitting the anonymized set of datasets to the third server, receiving, by the server, a set of mortality values corresponding to each user within the anonymized pool dataset.

3. The method of claim 2, further comprising identifying, by the server, one or more common identifiers within the anonymized pool dataset.

4. The method of claim 2, wherein the second server and the third server do not communicate without an intermediary processor.

5. The method of claim 1, wherein the genetic attribute is associated with at least one of BRCA1, BRCA2, and OCA2.

6. The method of claim 2, wherein the request further comprises an attribute associated with the mortality value.

7. The method of claim 6, wherein the anonymized pool dataset ranks each user of the anonymized pool dataset based on their respective mortality value.

8. The method of claim 1, wherein the identifiable information to be removed from the anonymized set of datasets is received from the client computing device.

9. The method of claim 1, wherein the genetic attribute comprises an attribute of a SNP of each user.

10. A computer system comprising:
a first server communicatively coupled with a client computing device via a graphical user interface displayed on the client computing device, the graphical user interface generated by the first server; and
a second server communicatively coupled only with the first server, wherein the first server comprises a non-transitory storage device having machine-executable instructions embodied thereon, wherein the machine-executable instructions, when executed by the first server, cause the first server to:
receive, from the client computing device, a request to generate an anonymized pool dataset, wherein the request comprises a number of a first set of users from which to generate the anonymized pool dataset, a selection of at least one genetic condition category, a threshold corresponding to a genetic attribute associated with each category, and a percentage of the first set of users associated with each genetic condition category;

query the second server to receive a set of datasets corresponding to the first set of users stored onto a database associated with the second server, wherein each dataset comprises data associated with each user comprising at least each respective user's genetic data, wherein the client computing device is prevented from communicating with the second server;

upon querying the second server, receive the set of datasets from the second server;

generate an anonymized set of datasets, wherein each dataset within the anonymized set of datasets corresponds to each user from the first set of users, and wherein the anonymized set of datasets does not contain any identifiable information corresponding to any of the first set of users;

execute a trained machine-learning model to identify each dataset within the anonymized set of datasets that satisfies the threshold corresponding to the genetic attribute associated with each genetic condition category from the at least one genetic condition category;

generate the anonymized pool dataset from the anonymized set of datasets, wherein the anonymized pool dataset comprises a second set of users from the first set of users who satisfy the threshold, wherein a number of the second set of users within the anonymized pool dataset corresponds to the number of the first set of users received from the client computing device, wherein each user from the second set of users is placed in the selected at least one genetic condition category that corresponds to each user's genetic data received from the client computing device, and wherein the number of the first set of users within each genetic condition category corresponds to the percentage of the first set of users associated with each genetic condition category received from the client computing device; and transmit the anonymized pool dataset to a third server configured to determine a mortality value associated with each user within the anonymized pool dataset and associated with the genetic attribute of each category.

11. The system of claim 10, wherein the first server is further configured to, upon transmitting the anonymized set of datasets to the third server, receive a set of mortality values corresponding to each user within the anonymized pool dataset.

12. The system of claim 10, wherein the first server is further configured to:
identify one or more common identifiers within the anonymized pool dataset.

13. The system of claim 11, wherein the second server and the third server do not communicate without an intermediary processor.

14. The system of claim 10, wherein the genetic attribute is associated with at least one of BRCA1, BRCA2, and OCA2.

15. The system of claim 11, wherein the request further comprises an attribute associated with the mortality value.

16. The system of claim 15, wherein the anonymized pool dataset ranks each user of the anonymized pool dataset based on their respective mortality value.

17. The system of claim 10, wherein the identifiable information to be removed from the anonymized set of datasets is received from the client computing device.

18. The system of claim 10, wherein the genetic attribute comprises an attribute of a SNP of each user.

\* \* \* \* \*